United States Patent [19]
Anand et al.

[11] Patent Number: 6,090,809
[45] Date of Patent: Jul. 18, 2000

[54] 1-(4-ARYLPIPERAZIN-1-YL)-ω-[N-(α,ω-DICARBOXIMIDO)]-ALKANES USEFUL AS URO-SELECTIVE $\alpha_1$-ADRENOCEPTOR BLOCKERS

[75] Inventors: Nitya Anand, Lucknow; Neelima Sinha; Sanjay Jain, both of Noida; Anita Mehta, Gurgaon; Anil Kumar Saxena, Lucknow, all of India

[73] Assignee: Ranbaxy Laboratories Limited, New Delhi, India

[21] Appl. No.: 09/203,855

[22] Filed: Dec. 2, 1998

Related U.S. Application Data

[62] Division of application No. 09/120,265, Jul. 21, 1998.

[30] Foreign Application Priority Data

Nov. 13, 1997 [IN] India .............................. 3260/DEL/97
Nov. 13, 1997 [IN] India .............................. 3261/DEL/97

[51] Int. Cl.[7] ...................... A61K 31/496; C07D 401/06; C07D 403/06
[52] U.S. Cl. .......................... 514/252; 514/326; 544/295; 544/360; 544/364; 544/372; 546/208
[58] Field of Search ..................... 544/360, 372; 514/252

[56] References Cited

U.S. PATENT DOCUMENTS 4,479,954 10/1984 Hirose et al. .
4,675,403 6/1987 Abou-Gharbia et al. .

FOREIGN PATENT DOCUMENTS

| 4594072 | 2/1974 | Australia . |
| 3678878 | 12/1979 | Australia . |
| 0 103 357 A2 | 3/1984 | European Pat. Off. . |
| 0 748 800 A2 | 12/1996 | European Pat. Off. . |
| 1368256 | 9/1974 | United Kingdom . |

OTHER PUBLICATIONS

Chilmonczyk, Zdzislaw, et al., "Conformational Flexibity of Serotonin1A Receptor Ligands from Crystallographic Data. Updated Model of the Receptor Pharmacophore", Chemical Abstracts 127:234308, vol. 127, No. 17 (1997).

Dimoglo, A.S. et al., "Study of Structure–Activity Relations in a Series of Buspirone Analogs Using an Electron–Topological Approach", Chemical Abstracts 129: 22916, vol. 129, No. 3 (1998).

Hays, Sheryl J., "Synthesis of Carbon–14 Labeled CI–926 and CI–927, New Antihypertensives," Chemical Abstracts 108:21844 vol. 108, No. 3 (1988).

Ishizumi, Kikuo et al., "Synthesis and Anxiolytic Activity of N–substituted Cyclic Imides (1R*,2S*,3R*,4S*)–N–[4–[4–(2–Pyrimidinyl)–1–Piperazinyl]Butyl]–2,3–Bicyclo[2.2.1]Heptanedicarboximide (Tandospirone) and Related Compounds", Chem. Pharm., Bull., vol. 39, No. 9 (1991) pp. 2288–2300.

Khadilkar, B.M. et al., "Synthesis and Pharmacology of Some 2–[3–(4–Aryl–1–Piperaxinyl)–Propyl]–1H–Benz[De]Isoquinolin–1,3(2H)–Diones", Chemical Abstracts 107:198046, vol. 107, No. 21 (1987).

Khadilkar, B.M., et al., "Synthesis and Hypotensive Activity of Some Succinimide Derivatives", Chemical Abstracts 119:27951, vol. 119, No. 3 (1993).

Ryan, M.J., et al., "CI–926 (3–[4–[4–(3–Methylphenyl)–1–Piperazinyl]Butyl]2,4–Imidazolinedione):Antihypertensive Profile and Pharmacology", Chemical Abstracts 105:164679, vol. 105, No. 19 (1986).

Wu, Yao–Hua, et al., "Psychosedative Agents. N–(4–Phenyl–1–Piperazinylalkyl)–Substituted Cyclic Imides", J. Med. Chem., vol. 12 (1969) pp. 876–881.

Wu, Y. et al. Journal of Medicinal Chemistry 1969, 12, 876–881.

*Primary Examiner*—Michael G. Ambrose
*Attorney, Agent, or Firm*—Jayadeep R. Deshmukh, Esq.

[57] ABSTRACT

Novel piperzine derivatives substituted on one nitrogen by an aromatic system and on the other nitrogen by (2,5-dioxopyrrolidin)-1-yl) alkanes or (2,6-dioxopiperidin-1-yl) alkanes have been found to exhibit selective $\alpha_{1A}$ adrenergic activity. The compounds are useful for treatment of disease conditions, such as peripheral vascular disease, congestive heart failure, hypertension and especially benign prostatic hypertrophy.

8 Claims, No Drawings

1-(4-ARYLPIPERAZIN-1-YL)-ω-[N-(α,ω-DICARBOXIMIDO)]-ALKANES USEFUL AS URO-SELECTIVE $\alpha_1$-ADRENOCEPTOR BLOCKERS This application is a division of U.S. application Ser. No. 09/120,265 filed Jul. 21, 1998.

1. FIELD OF THE INVENTION

The present invention relates to certain novel piperazine derivatives having protracted uro-selective $\alpha_1$-adrenoceptor antagonistic activity exceeding those of previously described compounds. The compounds of the present invention hold promise for treating benign prostatic hyperplasia (BPH). This invention also relates to methods for making the novel compounds, pharmaceutical compositions containing the compounds, and methods of treating benign prostatic hyperplasia using the compounds.

2. DESCRIPTION OF THE RELATED ART

A review in *J. Med. Chem.*, 1997, V.40, No.9, pp.1291–1315, describes the most important pharmacological options available at present in the treatment of benign prostatic hyperplasia. The two most successful therapies are based on α-adrenergic receptor antagonism and androgen levels modulation by 5α-reductase inhibitors. 5α-reductase inhibitors are of limited effectiveness in terms of immediate symptomatic and urodynamic relief. $\alpha_1$-antagonists appear to be much more effective and provide immediate subjective symptomatic improvements and are therefore the preferred modalities of treatment in the control of benign prostate hypertrophy. $\alpha_1$-adrenoceptors are also present in blood vessels and play an important role in the regulation of blood pressure. Thus, $\alpha_1$-adrenoceptor antagonists are of particular importance as they were originally developed as antihypertensive agents and are likely also to have a beneficial effect on lipid dysfunction and insulin resistance, which are commonly associated with essential hypertension.

The more important of the $\alpha_1$-adrenoceptor antagonists which are currently used in the management of BPH are shown below.

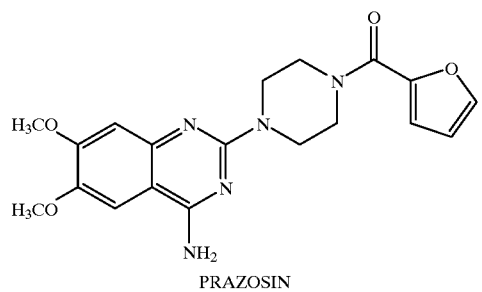

PRAZOSIN

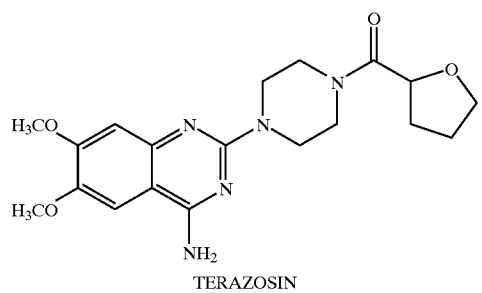

TERAZOSIN

-continued

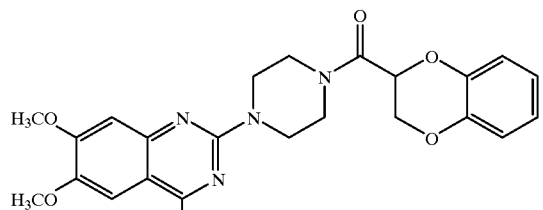

DOXAZOSIN

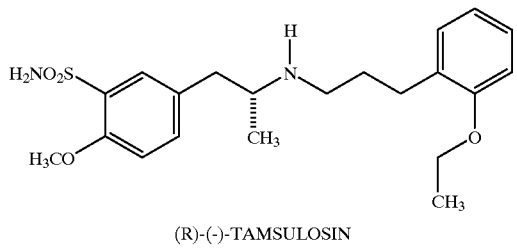

(R)-(-)-TAMSULOSIN

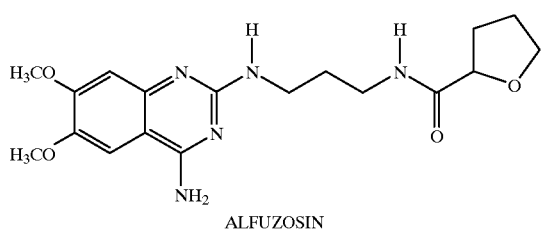

ALFUZOSIN

However, most of these known drugs are associated with vascular side effects (e.g., postural hypertension, syncope, dizziness, headaches, etc.) due to lack of selectivity of action between prostatic and vascular $\alpha_1$-adrenoceptors. Clearly, $\alpha_1$-adrenoceptor antagonists which have inherently greater selectivity for prostatic $\alpha_1$-adrenoceptors offer the potential of increased urodynamic benefits. This underscores the importance of the discovery of prostate-selective $\alpha_1$-adrenoceptor antagonists which will confer urodynamic improvement without the side effects associated with existing drugs.

Recently, it has been demonstrated that the prostate tissue of higher species like man and dog is overvalued by low affinity $\alpha_{1A}$-adrenoceptor subtype. This makes it possible to develop agents with selective action against these pathological urodynamic states. The present invention is directed to the development of novel $\alpha_1$-antagonists, namely, a new class of piperazine compounds, with greater selectivity of action against $\alpha_{1A}$-adrenoceptors and which would thus offer selective relief for prostate hypertrophy as well as essential hypertension.

There are many descriptions in the literature of the pharmacological activities associated with phenyl piperazines. *Eur. J. Med. Chem.-Chimica Therapeutica*, 1977, V. 12, No. 2, pp. 173–176, describes substituted the trifluoromethyl phenyl piperazines having cyclo-imido alkyl side chains shown below as anorectic agents with no CNS side effects.

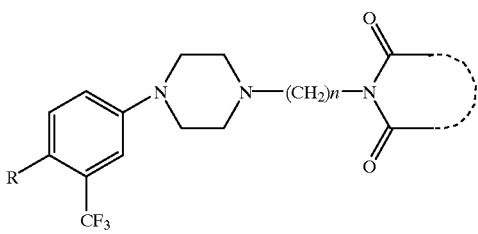

The synthesis and pharmacology of some 2-[3-(4-aryl-1-piperazinyl)propyl]-1H-benz[de]isoquinolin-1,3-(2H)-diones/2,5-pyrrolidinediones (*J. Indian Chem. Soc.,* 1986, V. LXIII, pp. 529–530), of N-(N⁴-aryl-N¹-piperozinylmethyl)-4-(4'-methoxyphenyl)piperidine-2,6-diones (*J. Indian Chem. Soc.,* 1978, v. LV, pp. 819–821), and of N-(N⁴-arylpiperazinylalkyl)-phthalimides (*J. Indian Chem. Soc.,* 1979, V. LVI, pp. 1002–1005), as shown below, have been reported. The compounds were shown to exhibit antihypertensive and CNS depressant activity in experimental animals.

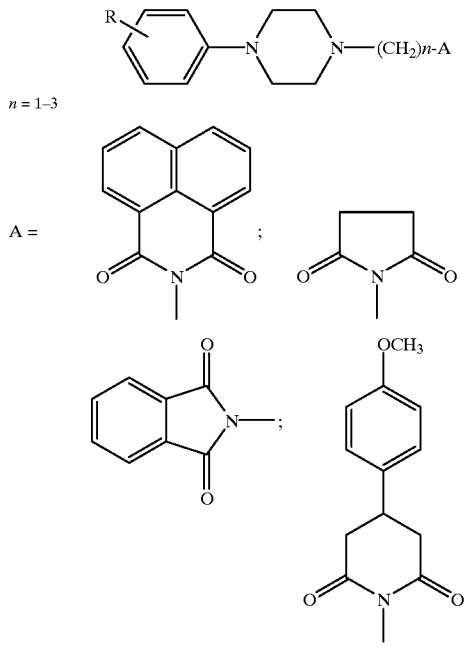

However, in those papers there is no mention of the adrenoceptor blocking activity of these compounds, and thus their usefulness in the treatment of benign prostate hyperplasia did not arise.

The earlier synthesis of various 1-(4-aryl-piperazin-1-yl)-3-(2-oxo-pyrrolidin-1-yl/piperidin-1-yl) alkanes and their usefulness as hypotensive and antischemic agents is disclosed in unpublished Indian patent applications DEL 496/95 (Mar. 3, 1995), DEL/500/95 (Mar. 21, 1995) and DEL/96/96 (Mar. 29, 1996) by the inventors herein. These compounds had low $\alpha_1$-adrenergic blocking activity (pKi~6 as compared to >8 of the known $\alpha_1$-antagonists such as prazosin), and practically no adrenoceptor sub-class selectivity for $\alpha_{1A}$ vs. $\alpha_{1B}$ or $\alpha_{1D}$ adrenoceptors. It has now been discovered that structural modification of these compounds from lactam to dioxo compounds, i.e., from 2-oxopyrrolidin to 2,5-dioxopyrrolidin and 2,6-dioxopiperidine, enhances the adrenoceptor blocking activity, and also greatly increases the selectivity for $\alpha_{1A}$ in comparison to $\alpha_{1B}$- adrenoceptor blocking activity, an essential requirement for compounds to be good candidates for treatment of BPH.

3. OBJECTS OF THE INVENTION

An object of the present invention, therefore, is to provide novel arylpiperazine derivatives that exhibit significantly greater $\alpha_{1A}$-adrenergic blocking potency than available with the known compounds in order to provide specific treatment for benign prostatic hyperplasia.

It is also an object of the invention to provide a method for synthesis of the novel compounds.

It is a further object of the invention to provide compositions containing the novel compounds which are useful in the treatment of benign prostatic hyperplasia.

4. SUMMARY OF THE INVENTION

The above-mentioned objectives are achieved by a novel class of piperazine derivatives of general Formula I below

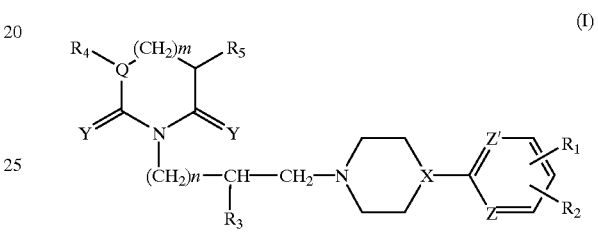

wherein Y is O or S; Q, X, Z and Z' are independently CH or N; m=0–3; n=0–4; $R_1$, $R_2$ are independently selected from: H, F, Cl, Br, $OCH_3$, $OC_2H_5$, $OCH_2CF_3$, $SCH_3$, $CH_3$, $C_2H_5$, $CF_3$, isopropyloxy, and cyclopropyl; $R_3$ is H, $R_6$, OH or $OR_6$; $R_6$ is a substituted or unsubstituted alkyl chain containing 1–6 carbon atoms; and $R_4$, $R_5$ are H, $C_{1-3}$ alkyl, substituted or unsubstituted phenyl, or a 5-membered spiro ring. Preferably, $R_1$ is H, $R_2$ is H, Cl or $CF_3$, $R_3$, $R_4$, and $R_5$=H, Y=O and Q=CH when m=0 and n=1; or $R_1$ is H, $R_2$ is $OCH_3$, $R_3$, $R_4$ and $R_5$=H, Y=O and Q=CH when m=0 and n=2.

Compounds within the scope of Formula I but having the structure of Formula II below

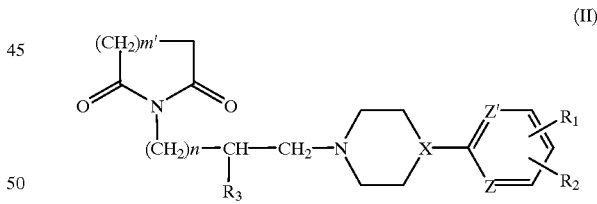

wherein n, X, Z Z' R'$_1$, $R_2$ and $R_3$ are as defined for Formula I, and wherein m'=1–4, are preferred as selective and potent $\alpha_{1A}$-adrenoceptor antagonistic activity over the $\alpha_{1B}$- and $\alpha_{1D}$-adrenoceptors. In Formula II, preferably $R_1$ is H, $R_2$ is H, Cl or $CF_3$, and $R_3$ is H when m'=1 and n=1; or $R_1$ is H, $R_2$ is $OCH_3$, and $R_3$ is H when m'=1 and n=2.

The present invention also provides pharmaceutical compositions for the treatment of benign prostatic hyperplasia. These compositions comprise an effective amount of at least one of the above compounds of Formula I, or preferably of Formula II, and/or an effective amount of at least one physiologically acceptable acid addition salt thereof, with a pharmaceutically acceptable carrier.

An illustrative list of particular compounds of the invention is given below:

| Compound No. | Chemical Name |
| --- | --- |
| 1. | 1-[4-(4-Fluorophenyl)piperazin-1-yl]-3-(2,5-dioxopyrrolidin-1-yl)propane |
| 2. | 1-[4-(2-Methoxyphenyl)piperazin-1-yl]-3-(2,5-dioxopyrrolidin-1-yl)propane |
| 3. | 1-[4-(3-Trifluoromethylphenyl)piperazin-1-yl]-3-(2,5-dioxopyrrolidin-1-yl)propane |
| 4. | 1-[4-(2-Pyridyl)piperazin-1-yl]-3-(2,5-dioxopyrrolidin-1-yl)propane |
| 5. | 1-[4-(3-Chlorophenyl)piperazin-1-yl]-3-(2,5-dioxopyrrolidin-1-yl)propane |
| 6. | 1-[4-(2-Pyrimidyl)piperazin-1-yl]-3-(2,5-dioxopyrrolidin-1-yl)propane |
| 7. | 1-[4-(3,4-Dimethylphenyl)piperazin-1-yl]-3-(2,5-dioxopyrrolidin-1-yl)propane |
| 8. | 1-[4-(Phenylpiperazin)-1-yl]-3-(2,5-dioxopyrrolin-1-yl)propane |
| 9. | 1-[4-(2-Methoxyphenyl)piperazin-1-yl]-4-(2,5-dioxopyrrolidin-1-yl)butane |
| 10. | 1-[4-(2-Methoxyphenyl)piperazin-1-yl]-2-(2,5-dioxopyrrolidin-1-yl)ethane |
| 11. | 1-[4-(3-Methoxyphenyl)piperazin-1-yl]-3-(2,5-dioxopyrrolidin-1-yl)propane |
| 12. | 1-[4-(4-Methoxyphenyl)piperazin-1-yl]-3-(2,5-dioxopyrrolidin-1-yl)propane |
| 13. | 1-[4-(2-Methoxyphenyl)piperazin-1-yl]-3-(2,6-dioxopiperidin-1-yl)propane |
| 14. | 1-[4-(4-Fluorophenyl)piperazin-1-yl]-3-(2,6-dioxopiperidin-1-yl)propane |
| 15. | 1-[4-(4-Chlorophenyl)piperazin-1-yl]-3-(2,6-dioxopiperidin-1-yl)propane |
| 16. | 1-[4-(3-Trifluoromethylphenyl)piperazin-1-yl]-3-(2,6-dioxopiperidin-1-yl)propane |
| 17. | 1-[4-(2-Fluorophenyl)piperazin-1-yl]-3-(2,6-dioxopiperidin-1-yl)propane |
| 18. | 1-[4-(2-Methylphenyl)piperazin-1-yl]-3-(2,6-dioxopiperidin-1-yl)propane |
| 19. | 1-[4-(2-Pyridyl)piperazin-1-yl]-3-(2,6-dioxopiperidin-1-yl)propane |
| 20. | 1-[4-(3-Chlorophenyl)piperazin-1-yl]-3-(2,6-dioxopiperidin-1-yl)propane |
| 21. | 1-[4-(3,4-Dimethylphenyl)piperazin-1-yl]-3-(2,6-dioxopiperidin-1-yl)propane |
| 22. | 1-[4-(2-Pyrimidyl)piperazin-1-yl]-3-(2,6-dioxopiperidin-1-yl)propane |
| 23. | 1-[4-(3-Methoxyphenyl)piperazin-1-yl]-3-(2,6-dioxopiperidin-1-yl)propane |
| 24. | 1-[4-(4-Methoxyphenyl)piperazin-1-yl]-3-(2,6-dioxopiperidin-1-yl)propane |
| 25. | 1-[4-(2-Methoxyphenyl)piperazin-1-yl]-4-(2,6-dioxopiperidin-1-yl)butane |
| 26. | 1-[4-(2-Methoxyphenyl)piperazin-1-yl]-3-[2,5-dioxo-3-phenyl-pyrolidin-1-yl]propane |
| 27. | 1-[4-(Phenyl)piperazin-1-yl]-3-[2,5-dioxopiperidin-1-yl]propane |

5. DETAILED DESCRIPTION OF THE INVENTION

5a. Synthesis of the Compounds of the Invention

The compounds of the present invention may be prepared by one of the reaction sequences (Schemes I, II & III) shown below to yield compounds of Formula II with the $R_1$, $R_2$, $R_3$, $R_4$, $R_5$, $R_6$, m, n, Z, Z', Q and Y groups as defined above. The starting materials for Schemes I, II and III may be suitably adapted to produce the more general compounds of Formula I.

Scheme—I

Scheme-I shows the synthesis of compounds of the Formula II in which $R_1$, $R_2$, $R_3$, $R_4$, $R_5$, $R_6$, m', n, Z, Z', Q, X, and Y are as defined earlier. The preparation comprises condensing α,ω-dicarboximides of Formula III with 1-(4-arylpiperazin-1-yl)-ω-chloroalkanes of Formula IV, in the presence of a base and an organic solvent at a temperature ranging from 80–150° C. for a period varying between 8–24 hours to produce the corresponding 1-(4-arylpiperazin-1-yl)-ω-[N-(α,ω-dicarboximido)]alkanes of the Formula II where $R_1$ and $R_2$ have the meanings given above. Phase transfer catalysts, preferably tetrabutylammonium bromide, are particularly useful in catalysing the reaction.

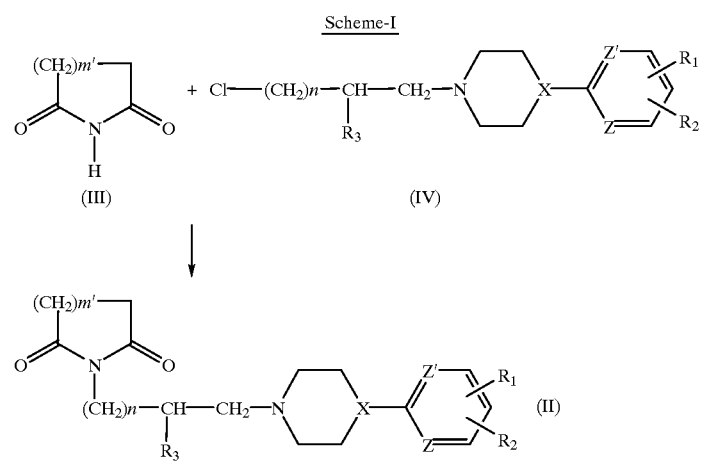

Scheme—II

The compounds of Formula II can also be prepared by condensation of the piperazines of the Formula V with the anhydrides of Formula VI wherein $R_1$, $R_2$, $R_3$, Y, Z, Z', X, and m' are as defined above.

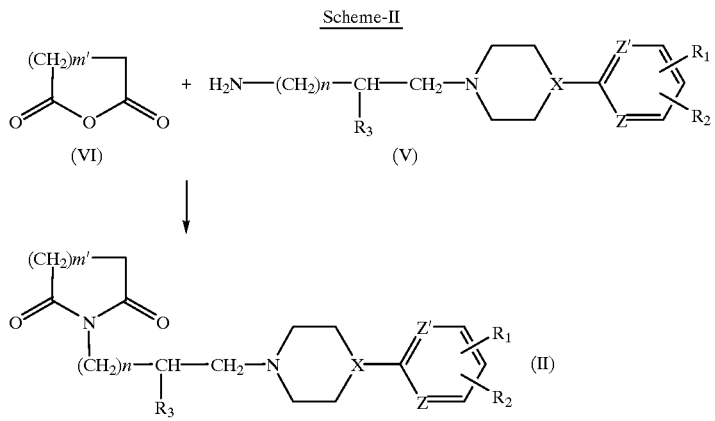

Scheme—III

The compounds of Formula II can also be prepared by alkylation of the α,ω-dicarboximide moiety with α,ω-dihaloalkanes followed by condensation of 1-(ω-haloalkyl) dicarboximide thus obtained (Formula VII) with 1-arylpiperazines (Formula VIII) as shown below, wherein $R_1$, $R_2$, $R_3$, Y, Z, Z', X, m' and n are as defined above. The reaction is preferably carried out in the presence of a base and an organic solvent at a temperature ranging from 60–100° C. for a period varying between 10–24 hours to produce the corresponding 1-(4-arylpiperazin-1-yl)-ω-[N-(α,ω-dicarboximido)]alkanes of Formula II. Phase transfer catalysts, more preferably tetrabutylammonium bromide and potassium iodide, are useful in catalysing the reaction.

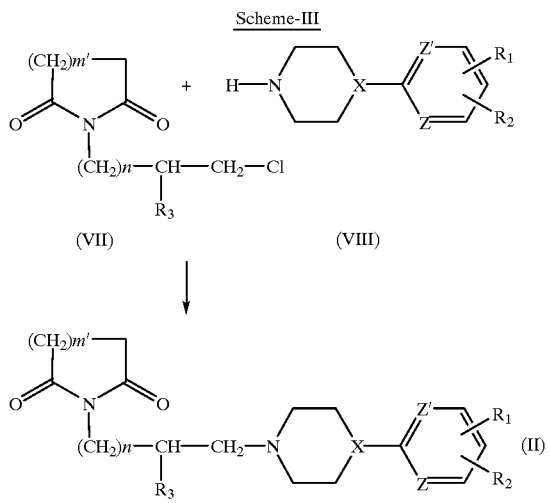

In the above Schemes, where specific bases, acids, solvents, phase transfer catalysts, etc., are mentioned, it is to be understood that other acids, bases, solvents, phase transfer catalysts, etc., known to those skilled in the art may also be used. Similarly, the reaction temperature and duration of the reactions may be adjusted according to the desired needs.

The starting piperazines of the Formulas IV, V and VIII are known in the art and may be synthesized by the procedures described in Kiritzy, J. A., et al., *J. Med. Chem.,* 1978, V. 21, p. 1301; U.S. Pat. No. 3,637,705 (Abbott, 1972); FR 2,179,491 (1973); Aggarwal S. K., et al., *Ind. J. Chem.,* 1982, V.21B, pp. 435–439; and U.S. Pat. No. 2,922,788 (Parcell, 1960).

5b. Pharmacological Testing Results

The affinity of the compounds of the invention for each subtype of α-adrenoceptor can be assessed by receptor binding assays (RBA's) described in the examples given below. It should be noted that the identification and characterization of the foregoing receptors is still in progress and that their types and subtypes are subject to review and refinement.

Receptor binding and in vitro functional assay studies described below indicated that the compounds of the present invention possess selective and potent $\alpha_{1A}$ adrenoceptor antagonistic activity over the $\alpha_{1B}$ and $\alpha_{1D}$ adrenoceptors. The present invention also provides a method to demonstrate the selective affinity of the compounds for prostatic tissues over vascular tissues. Further, the examples presented below describe a method to treat BPH in mammals wherein the test compounds alleviated pressure at dosages which did not result in significant change in blood pressure. Several of the compounds of present invention demonstrated manifest selectivity for prostatic tissues in comparison to known compounds, such as terazosin, doxazosin, etc. The compounds of the present invention also lowered the blood pressure with prolonged duration of action. The compounds of the present invention have been demonstrated to be useful for treating warm blooded animals and mammals. These compounds can be administered orally or parenterally in suitable pharmaceutical compositions.

Preferred compounds of the invention are 1-[4-(2-methoxyphenyl)piperazin-1-yl]-3-(2,5-dioxopyrrolidin-1-yl)propane (Compound No. 2), 1-[4-(2-methoxyphenyl)piperazin-1-yl]-4-(2,5-dioxopyrrolidin-1-yl)butane (Compound No. 9), and 1-[4-(2-methoxyphenyl)piperazin-1-yl]-3-(2,6-dioxopiperidin-1-yl)propane (Compound No. 13).

Pharmaceutically acceptable, non-toxic, acid addition salts of the compounds of the present invention having the utility of the free bases of Formulas I and II may be formed with inorganic or organic acids, by methods well known in the art and may be used in place of the free bases. Representative examples of suitable acids for formation of such acid addition salts are malic, fumaric, benzoic, ascorbic, pamoic, succinic, bismethylene salicylic, methanesulfonic, ethane disulfonic, acetic, propionic, tartaric, salicylic, citric, gluconic, aspartic, stearic, palmitic, itaconic, glycolic, p-aminobenzoic, glutamic, benzenesulfamic, phosphoric, hydrobromic, sulfuric, cyclohexylsulfamic, hydrochloric and nitric acids.

The present invention also includes within its scope prodrugs of the compounds of Formulas I and II. In general, such prodrugs will be functional derivatives of these compounds which are readily converted in vivo into the defined compounds. Conventional procedures for the selection and preparation of suitable prodrugs are known.

The invention also includes the enantiomers, diasteromers, N-oxides and pharmaceutically acceptable salts of these compounds, as well as metabolites having the same type of activity. The invention further includes pharmaceutical compositions comprising the molecules of Formula I and II, or prodrugs, metabolites, enantiomers, diasteromers, N-oxides, or pharmaceutically acceptable salts thereof, in combination with a pharmaceutically acceptable carrier and optionally included excipients.

In yet another aspect, the invention is directed to methods for selectively blocking $\alpha_{1A}$ receptors by delivering in the environment of said receptors, e.g., to the extracellular medium (or by administering to a mammal possessing said receptors), an effective amount of the compounds of the invention.

The invention will now be illustrated by the following non-limiting examples.

Preparation of 1-[4-(4-Fluorophenyl)piperazin-1-yl]-3-[2,5-dioxopyrrolidin-1-yl]propane (Compound No. 1)

Scheme-I: A mixture of 2,5-dioxopyrrolidine (0.500 g, 5 mmol), 1-[4-(4-fluorophenyl)-piperazin-1-yl]-3-chloropropane (1.28 g, 5 mmol), potassium carbonate (0.502 g, 3.75 mmol) and tetrabutylammonium bromide (0.322 g, 1 mmol) in acetone (25 ml) was refluxed for 16 hours at 80° C. with stirring. The solvent was evaporated off in vacuo and the residue was suspended in water (80 ml). The aqueous solution was extracted with chloroform (3×50 ml), and the organic layers combined, washed with water (2×50 ml), dried over $Na_2SO_4$ and evaporated in vacuo to give the title compound. The product was purified by column chromatography over flash silica gel using chloroform-methanol (98:2) as eluent; yield 1.00 g (65%), oil.

Scheme-II: 1-amino-3-[4-(4-fluorophenyl)piperazin-1-yl]propane (0.700 g, 2.95 mmol) and succinic anhydride (0.295 g, 2.95 mmol) were refluxed in pyridine (10 ml) for 10 hours. Acetic anhydride (2 ml, excess) was added and the mixture was further refluxed for 5 hours. Solvent was remove din vacuo and the residue was suspended in water and extracted with chloroform (2×25 ml). Organic layers were combined, washed with water (2×25 ml), dried over $Na_2SO_4$ and concentrated. The compound was purified by column chromatography over flash silica gel using chloroform-methanol (98:2) as eluent; yield 0.436 g (46%), oil.

Scheme-III: A mixture of 1-chloro-3-(2,5-dioxopyrrolidin-1-yl) propane (1.54 g, 8.80 mmol), 1-(4-fluorophenyl)piperazine (1.58 g, 8.80 mmol), potassium carbonate (1.21 g, 8.80 mmol) and potassium iodide (0.146 g, 0.88 mmol) in N,N-dimethylformamide (25 ml) was heated at 100° C. for 18 hours. Solvent was evaporated under reduced pressure. Residue was shaken with water (25 ml), extracted with chloroform (2×25 ml), and the organic layers combined, washed with water (2×20 ml), dried over $Na_2SO_4$ and concentrated to give an oil which was purified by column chromatography over flash silica gel using chloroform-methanol (98:2) as eluent; yield 2.00 g (71%), oil.

The hydrochloride salt of 1-[4-(4-fluorophenyl)piperazin-1-yl]-3-(2,5-dioxopyrrolidin-1-yl)-propane (Compound No. 1) was formed in quantitative yield by the addition of ethereal hydrogen chloride solution to a methanolic solution of the free base and the resultant precipitate was collected by filtration; m.p. 246–247° C.

Preparation of 1-[4-(2-methoxyphenyl)piperazin-1-yl]-3-[2,5-dioxopyrrolidin-1-yl]propane (Compound No. 2)

Scheme-I: A mixture of 2,5-dioxopyrrolidine (3.68 g, 37.24 mmol), 1-[4-(2-methoxyphenyl)-piperazin-1-yl]-3-chloropropane (10.0 g, 37.24 mmol), potassium carbonate (7.70 g, 55.8 mmol) and tetrabutylammonium bromide (2.38 g, 7.4 mmol) in acetone (100 ml) was refluxed for 12 hours at 80° C. with stirring. The solvent was evaporated off in vacuo and the residue was taken up in water (80 ml). The aqueous solution was extracted with chloroform (3×50 ml) and the organic layers combined, washed with water 2×50 ml), dried over $Na_2SO_4$ and evaporated in vacuo to give the title compound. The product was purified by column chromatography over flash silica gel using chloroform-methanol (99:1) as eluent; yield 8.00 g (65%) in oil. The hydrochloride salt was prepared by the method described above; mp 199–202° C.

Scheme-III: A mixture of 1-chloro-3-(2,5-dioxopyrrolidin-1-yl) propane (28.00 gm, 159.5 mmol), 1-(2-methoxyphenyl)piperazin hydrochloride (36.45 g, 159.5 mmol), potassium carbonate (44.03 g, 319.0 mmol) and potassium iodide (1.58 g, 9.57 mmol) in N,N-dimethylformamide (115 ml) was heated at 80° C. for 17 hours and the solvent was evaporated under reduced pressure. Residue was suspended in ethyl acetate (600 ml), washed with water (5×100 ml.) and dried over $Na_2SO_4$ and concentrated to give an oil which was purified by column chromatography over silica gel (100–200 mesh) using chloroform-methanol (99:2) as eluent; yield 55.1 g, (80%), oil. The hydrochloride salt of this product was formed in the manner described above; mp. 199–202° C.

1-Chloro-3-(2,5-dioxopyrrolidin-1-yl)propane can be prepared by the reaction of 2,5-dioxopyrrolidine and 1-bromo-3-chloropropane in the presence of potassium carbonate and tetrabutylammonium bromide in acetone.

Preparation of 1-[4-(2-methoxyphenyl)piperazin-1-yl]-3-[2,5-dioxopyrrolidin-1-yl]butane (Compound No. 9)

Scheme-III: A mixture of 1-chloro-4-(2,5-dioxopyrrolidin-1-yl)butane (11.0 g, 58.04 mmol), 1-[2-methoxyphenyl)piperazin hydrochloride (12.99 g, 56.85 mmol), potassium carbonate (16.02 g, 116.09 mmol) and potassium iodide (0.577 g, 3.48 mmol) in N,N-dimethylformamide (45 ml) was stirred at 100° C. for 18 hours. N,N-dimethylformamide was evaporated at reduced pressure and the residue was taken up in water (100 ml) and extracted with chloroform (2×100 ml). The extracts were dried over $Na_2SO_4$ and concentrated under reduced pressure to give 1-[4-(2-methoxyphenyl)piperazine-1-yl]-4-(2,5-dioxopyrrolidin-1-yl)butane as an oil which was purified by column chromatography over silica gel (230–400 mesh) using chloroform-methanol (98.2) as eluent; yield 18.00 g, (92%), oil. Hydrochloride salt was prepared by the method described above; mp 218–220° C.

1-Chloro-4-(2,5-dioxopyrrolidin-1-yl)butane can be prepared by the reaction of 2,5-dioxopyrrolidine and 1-bromo-4-chlorobutane in the presence of potassium carbonate and tetrabutylammonium bromide in acetone.

Preparation of 1-[4-(2-methoxyphenyl)piperazin-1-yl]-3-[2,6-dioxopiperidin-1-yl)propane (Compound No. 13)

Scheme-I: A mixture of 2,6-dioxopiperidine (2.60 g, 23.02 mmol), 1-[4-(2-methoxyphenyl)-piperazin-1-yl]-3- chloropropane (6.18 g, 23.02 mmol), potassium carbonate (2.38 g, 17.27 mmol) and tetrabutylammonium bromide (1.48 g, 4.60 mmol) in acetone (80 ml) was refluxed for 16 hours at 80° C. with stirring. The solvent was evaporated off in vacuo and the residue suspended in water (60 ml), extracted with chloroform (3×40 mmol) and the organic layers combined, washed with water (2.40 ml), dried over anhydrous $Na_2SO_4$ and evaporated in vacuo to give the title compound. The product was purified by column chromatography over flash silica gel (230–400 mesh) using chloroform-methanol (98:1) as eluent; yield 3.58 g (45%), oil.

The hydrochloride salt was prepared in the quantitative yield by the method described above; m.p. 206–210° C.

Scheme-III: A mixture of 1-chloro-3-(2,6-dioxopiperidin-1-yl)propane (22.06 gm, 116.40 mmol), 1-(2-methoxyphenyl)piperazine (21.90 g, 114.06 mmol), potassium carbonate (16.06 g, 116.40 mmol) and potassium iodide (1.16 g, 6.98 mmol) in N,N-dimethylformamide (90 ml), was heated at 80° C. for 17 hrs. and the solvent was evaporated under reduced pressure. Residue was dissolved in ethyl acetate (400 ml), washed with water (5×100 ml) and dried over $Na_2SO_4$ and concentrated to given an oil which was purified by column chromatography over silica gel (100–200 mesh) using chloroform-methanol (99:1) as eluent; yield 33.8 g, (86%), oil. The hydrochloride salt was prepared in the quantitative yield by the addition of excess ethereal hydrogen chloride solution to a methanolic solution of the free base and collected by filtration of the resultant precipitate; m.p. 206–210° C.

An illustrative list of the compounds of the invention which were synthesized by one or more of the above described methods is now given.

1-[4-(4-Fluorophenyl)piperazin-1-yl]-3-(2,5-dioxopyrrolidin-1-yl)propane hydrochloride; m.p. 246–247° C.

1-[4-(2-Methoxyphenyl)piperazin-1-yl]-3-(2,5-dioxopyrrolidin-1-yl)propane hydrochloride; m.p. 199–202° C.

1-[4-(3-Trifluoromethylphenyl)piperazin-1-yl]-3-(2,5-dioxopyrrolidin-1-yl)propane hydrochloride; m.p. 218–220° C.

1-[4-(2-Pyridyl)piperazin-1-yl]-3-(2,5-dioxopyrrolidin-1-yl)propane hydrochloride; m.p. 261–262° C.

1-[4-(3-Chlorophenyl)piperazin-1-yl]-3-(2,5-dioxopyrrolidin-1-yl)propane hydrochloride; m.p. 230–231° C.

1-[4-(2-Pyrimidyl)piperazin-1-yl]-3-(2,5-dioxopyrrolidin-1-yl)propane hydrochloride; m.p. 196–198° C.

1-[4-(3,4-Dimethylphenyl)piperazin-1-yl]-3-(2,5-dioxopyrrolidin-1-yl) propane hydrochloride; m.p. 244–246° C.

1-[4-(Phenyl)piperazin-1-yl]-3-(2,5-dioxopyrrolidin-1-yl)propane hydrochloride; m.p. 258–259° C.

1-[4-(2-Methoxyphenyl)piperazin-1-yl]-4-(2,5-dioxopyrrolidin-1-yl)butane hydrochloride; m.p. 219–220° C.

1-[4-(2-Methoxyphenyl)piperazin-1-yl]-2-(2,5-dioxopyrrolidin-1-yl)ethane hydrochloride; m.p. 232–234° C.

1-[4-(3-Methoxyphenyl)piperazin-1-yl]-3-(2,5-dioxopyrrolidin-1-yl)propane hydrochloride; m.p. 199–201° C.

1-[4-(4-Methoxyphenyl)piperazin-1-yl]-3-(2,5-dioxopyrrolidin-1-yl)propane hydrochloride; m.p. 240–242° C.

1-[4-(2-Methoxyphenyl)piperazin-1-yl]-3-(2,6-dioxopiperidin-1-yl)-propane hydrochloride; m.p. 206–210° C.

1-[4-(4-Fluorophenyl)piperazin-1-yl]-3-(2,6-dioxopiperidin-1-yl)propane; m.p. 200–202° C.

1-[4-(4-Chlorophenyl)piperazin-1-yl]-3-(2,6-dioxopiperidin-1-yl)propane hydrochloride; m.p. 206–208° C.

1-[4-(3-Trifluoromethylphenyl)piperazin-1-yl]-3-(2,6-dioxopiperidin-1-yl)propane hydrochloride; m.p. 228–229° C.

1-[4-(2-Fluorophenyl)piperazin-1-yl]-3-(2,6-dioxopiperidin-1-yl)propane hydrochloride; m.p. 215–216° C.

1-[4-(2-Methylphenyl)piperazin-1-yl]-3-(2,6-dioxopiperidin-1-yl)propane hydrochloride; m.p. 206–207° C.

1-[4-(2-Pyridyl)piperazin-1-yl]-3-(2,6-dioxopiperidin-1-yl)propane hydrochloride; m.p. 244–245° C.

1-[4-(3-Chlorophenyl)piperazin-1-yl]-3-(2,6-dioxopiperidin-1-yl)propane hydrochloride; m.p. 214–215° C.

1-[4-(3,4-Dimethylphenyl)piperazin-1-yl]-3-(2,6-dioxopiperidin-1-yl)propane hydrochloride; low melting hygroscopic.

1-[4-(2-Pyrimidyl)piperazin-1-yl]-3-(2,6-dioxopiperidin-1-yl)propane hydrochloride; m.p. 195–196° C.

1-[4-(3-Methoxyphenyl)piperazin-1-yl]-3-(2,6-dioxopiperidin-1-yl)propane hydrochloride; m.p. 196–197° C.

1-[4-(4-Methoxyphenyl)piperazin-1-yl]-3-(2,6-dioxopiperidin-1-yl)propane hydrochloride; m.p. 218–220° C.

1-[4-(2-Methoxyphenyl)piperazin-1-yl]-4-(2,6-dioxopiperidin-1-yl)butane hydrochloride; m.p. 190–192° C.

1-[4-(2-Methoxyphenyl)piperazin-1-yl]-3-(2,5-dioxo-3-phenylpyrrolidin-1-yl]propane hydrochloride; m.p. 171–172° C.

1-[4-(Phenyl)piperadin-1-yl]-3-(2,5-dioxopyrrolidin-1-yl]propane hydrochloride; m.p. 208–209° C.

All the melting points reported above are uncorrected and measured by an open capillary method using Buchi 535.

Receptor Binding Assay

In vitro receptor binding

Receptor binding assays (RBA's) were performed for native $\alpha_1$-adrenoceptors. Rat submaxillary and rat liver membrane preparations were used to assess the affinity for $\alpha_{1A}$ and $\alpha_{1B}$ subtypes, respectively. Aliquots of membrane protein (100–200 mg) were incubated in a final volume of 250 ml assay buffer (50 mM Tris, 0.5 mM EDTA at pH 7.4) with 0.5 nM [$^3$H] prazosin for 60 mins at 28° C. Reaction was stopped by rapid filtration on Millipore filters. Filters were dried and bound radioactivity counted. Non-specific binding was determined in the presence of 0.3 mM prazosin. Protein was assayed according to the method of protein estimation by Lowry, O. H. et al., *J. Biol. Chem.*, V. 193, pp. 265–275 (1951). Results are listed in Table 1.

TABLE 1

| Compound No. | RBA (Ki nM) $\alpha_{1A}$ | $\alpha_{1B}$ | In Vitro Functional Assay (pK$_B$) $\alpha_{1A}$ | $\alpha_{1B}$ | $\alpha_{1D}$ | In Vivo BP Fall in mmHg | Duration in min. |
|---|---|---|---|---|---|---|---|
| Compound 1 | >2500 | 1000 | 7.1 | 7.0 | 6.8 | 5.0 | 15.0 |
| Compound 2 | 19 | 244 | 8.7 | 7.6 | 7.3 | 25 | 120.0 |
| Compound 3 | 1500 | 1000 | — | 7.2 | 5.0 | — | — |
| Compound 4 | 1660 | 2100 | — | — | 5.6 | — | — |
| Compound 5 | 106 | 175 | 5.3 | 5.3 | 7.0 | — | — |
| Compound 6 | 1140 | >2500 | 4.7 | 5.3 | 6.5 | — | — |
| Compound 7 | 450 | 282 | 6.4 | 6.7 | 6.5 | — | — |
| Compound 8 | 57 | 590 | 7.5 | — | 6.6 | — | — |
| Compound 9 | 1 | 35 | 9.0 | 8.0 | 8.3 | 46 | >180 |
| Compound 10 | 1600 | 2350 | 6.9 | 6.7 | 6.9 | — | — |
| Compound 11 | >2500 | >2500 | — | — | — | — | — |
| Compound 12 | >2500 | >2500 | — | — | — | — | — |
| Compound 13 | 3 | 168 | 8.6 | 8.0 | 7.9 | 50.0 | >180 |
| Compound 14 | 67 | 192 | 8.4 | 7.4 | 7.1 | 20.0 | 60.0 |
| Compound 15 | 520 | 201 | 6.7 | 6.0 | 6.2 | — | — |
| Compound 16 | 345 | 765 | 6.5 | — | 6.9 | — | — |
| Compound 17 | 21 | 396 | 8.0 | 7.1 | 7.9 | 50.0 | 120.0 |
| Compound 18 | 9 | 267 | 8.2 | 5.5 | 8.5 | 40.0 | >150 |
| Compound 19 | 164 | >2500 | 6.4 | — | 6.7 | — | — |
| Compound 20 | 22 | 113 | 7.5 | — | 7.6 | — | — |
| Compound 21 | 2130 | 176 | 6.5 | 6.7 | 6.5 | — | — |
| Compound 22 | >2500 | >2500 | 6.4 | — | 7.0 | — | — |
| Compound 23 | 2170 | 940 | — | — | — | — | — |
| Compound 24 | <2500 | >2500 | — | — | — | — | — |
| Compound 25 | 1.6 | 7.5 | — | — | — | — | — |
| Compound 26 | 30 | 600 | — | — | — | — | — |
| Compound 27 | 1300 | 2000 | — | — | — | — | — |

In vitro Functional Studies
In vitro $\alpha_1$-Adrenoceptor selectivity

In order to study selectivity of action of the present compounds towards different α-adrenoceptor subtypes, the ability of these compounds to antagonize $\alpha_1$-adrenoceptor agonist induced contractile response of aorta ($\alpha_{1D}$), prostate ($\alpha_{1A}$) and spleen ($\alpha_{1B}$) was studied. Aorta, prostate and spleen tissues were isolated from urethane anaesthetized (1.5 gm/kg) male wistar rats. Isolated tissues were mounted in organ bath containing Krebs Henseleit buffer of the following composition (mM): NaCl 118; KCl 4.7; CaCl$_2$ 2.5; MgSO$_4$.7H$_2$O 1.2; NaHCO$_3$ 25; KH$_2$PO$_4$ 1.2; glucose 11.5. Buffer was maintained at 37° C. and aerated with a mixture of 95% O$_2$ and 5% CO$_2$. A resting tension of 2 g (aorta) or 1 g (spleen and prostate) was applied to tissues. Contractile response was monitored using a force displacement transducer and recorded on chart recorders. Tissues were allowed to equilibrate for 2 hours. At the end of equilibration period, concentration response curves to norepinephrine (aorta) and phenylephrine (spleen and prostate) were obtained in the absence and presence of the tested compound (at concentrations of 0.1, 1 and 10 μM). Antagonist affinity was calculated and expressed as pK$_B$ values in Table 1.

In vitro Receptor Selectivity

Selectivity of action of the present compounds was tested against a range of different receptors, e.g., $\beta_1$- and $\alpha_2$-adrenergic, muscarinic cholinergic, serotoninergic (5-HT$_{2A}$), histaminergic (H$_1$), angiotensin II, endothelin (ET$_A$ and $_B$,), as well as calcium and potassium channels. Rat aorta was used to study the effect of the compounds on 5-HT$_{2A}$, ET$_A$, calcium and potassium channels. Angiotensin II receptor antagonistic activity was studied in rabbit aorta. Muscarinic cholinergic receptor and ET$_B$ receptor antagonistic activity was studied in rat trachea, while guinea pig trachea was used to study H$_1$ receptor antagonistic activity. Electrically stimulated rat vas deferens was used to investigate the effect of $\alpha_2$-adrenoceptors, while $\beta_1$-adrenoceptor antagonistic activity was studied using electrically stimulated rat ventricular strips. Results of this selectivity study is shown in (Table 2).

TABLE 2

| Selectivity Study Receptor Type pK$_B$ | | | |
|---|---|---|---|
| | Compound 2 | Compound 9 | Compound 13 |
| $\alpha_2$-adrenergic | NE | NE | NE |
| β-adrenergic | 4.2 | — | 5.1 |
| Muscarinic | 5.0 | 5.0 | 5.5 |
| H$_1$-Histaminergic | 5.3 | 5.4 | 5.7 |
| 5-HT$_{2A}$ | 7.6 | 7.9 | 8.0 |
| ET$_A$ | — | 4.3 | 4.3 |
| ET$_B$ | — | 5.4 | 4.9 |
| Angiotensin II | — | 5.6 | 5.3 |
| Calcium Channel | NE | NE | NE |
| Potassium Channel | NE | NE | 5 |

NE: No effect
(—): Not tested

In vivo Antihypertensive Effect

Antihypertensive effect of selected compounds according to the invention were studied for their ability to lower blood pressure in anaesthetized and conscious normotensive and spontaneously hypertensive rats via intravenous, oral and intraduodenal routes. Results are shown in Tables 1 and 3.

Anaesthetized Normotensive Rats

Intravenous Route

Male wistar rats were anasthetized with urethane (2.5 g/kg). Femoral vein and carotid artery were cannulated. Blood pressure and heart rate were recorded using Statham pressure transducer. Data was recorded on Grass polygraph as well as using online data acquisition system (Buxco AT).

Intravenously administered compounds of the invention were initially tested at 0.3 mg/kg over a period of 3 hours for their effect on blood pressure and the results are shown in Table 1. For a select few of the compounds, the blood pressure lowering effect upon intravenous administration was also studied at dosages of 0.03, 0.1, 0.3, and 1 mg/kg.

Intraduodenal Route

Male wistar rats were fasted for 18 hours. Rats were anaesthetized with urethane. Femoral vein and carotid artery were cannulated. A catheter was placed in the duodenum following lapratomy. The compounds of the present invention (at dosages of 0.3, 1, 3 and 10 mg/kg) were administered in the duodenum and blood pressure was monitored for 3 hours. Results are recorded in Table 3.

TABLE 3

Effect on mean arterial pressure in anaesthetized normotensive rats.

| Compound No. | Dose (mg/kg) | Mean Arterial Pressure (% Change from basal) | Duration of Action |
|---|---|---|---|
| Compound 2 | 1 | −19 | >2.5 hr |
|  | 3 | −43 | >2.5 hr |
|  | 10 | −42 | >2.5 hr |
| Compound 9 | 1 | −19 | >3.0 hr |
|  | 3 | −53 | >3.0 hr |
|  | 10 | −57 | >3.0 hr |
| Compound 13 | 1 | −32 | <3.0 hr |
|  | 3 | −40 | >3.0 hr |
|  | 10 | −42 | >3.0 hr |

Conscious Normotensive Rats

Femoral artery of normotensive male wistar rats, maintained on an overnight light diet, were catheterized under pentobarbitone anaesthesia (35 mg/kg). Femoral artery catheter was exteriorized through the neck region for blood pressure recording. Compounds of the present invention (at dosages of 0.1, 0.3 and 1 mg/kg) were administered 24 hours following surgery through oral route in the form of gavage to overnight fasted rats. Blood pressure and heart rate were recorded with the help of Statham pressure transducer on a Grass polygraph and the results are shown in Table 4.

TABLE 4

Effect on systolic blood pressure in conscious spontaneously hypertensive rats

| Compound No. | Dose (mg/kg) | Systolic Pressure (% Change from basal) (at 6 hours) |
|---|---|---|
| Compound 2 | 1 | −7.0 |
|  | 3 | −12.0 |
|  | 10 | −13.0 |
|  | 30 | −17.0 |
| Compound 9 | 1 | −0.4 |
|  | 3 | −7.0 |
|  | 10 | −24.0 |
|  | 30 | −25.0 |
| Compound 13 | 1 | −7.0 |
|  | 3 | −18.0 |
|  | 10 | −19.0 |
|  | 30 | −14.0 |

Conscious Spontaneously Hypertensive Rats

Spontaneously hypertensive rats weighing between 250–300 g were used in this study. Rats were fasted overnight. Blood pressure was monitored from tail artery using semi-automatic noninvasive blood pressure monitoring apparatus. Compounds of the present invention (at dosages of 1, 3, 10, and 30 mg/kg) were administered orally. Blood pressure was monitored prior to and 1.5, 4, 6 and 24 hours after drug administration. Results are shown in Table 5.

TABLE 5

Effect on mean arterial blood pressure in conscious freely moving normotensive rats.

| Compound No. | Dose (mg/kg) | Mean Arterial Pressure (% Change from basal) |
|---|---|---|
| Compound 2 | 3 | −14 |
|  | 10 | −10 |
| Compound 9 | 1 | −4 |
|  | 10 | −11 |
| Compound 13 | 1 | −5 |
|  | 3 | −10 |

In Vivo Selectivity Study

Male mongrel dogs (12–20 Kg) were anaesthetized with pentobarbitone sodium (35 mg/kg, iv). Trachea was incubated for artificial respiration. Femoral artery and femoral vein were cannulated for recording blood pressure and for administration of drug solutions, respectively. Blood pressure was recorded on a polygraph through a pressure transducer. A paramedian incision was made lateral to the penis and the bladder was exposed. Urine was drained through a cannula put directly into the bladder and it was guided into the urethra gently and was placed at the prostatic urethra. Balloon was inflated with 2 cc air and its placement was confirmed by digital pressure. Intraurethral pressure was recorded on the polygraph through a pressure transducer. Graded dose response relationship of phenylephrine (1–16 $\mu$g/kg, iv) was obtained on prostatic pressure and blood pressure, prior to administration of the compounds of the present invention. Compounds 2, 9, and 13 (at dosages of 0.01, 0.03, 0.1, and 0.3 mg/kg) were administered intravenously 10 min before obtaining phenylephrine dose response curves. Results were analyzed and pseudo $pK_B$ values were calculated as described in Kenny et al (1996). Results are shown in Table 6.

TABLE 6

Effect on blood pressure and intraurethral pressure in anaesthetized dogs pseudo $pK_B$

| | Blood Pressure | Intraurethral Pressure |
|---|---|---|
| Compound 2 | 6.9 | 7.60 |
| Compound 9 | 7.4 | 7.9 |
| Compound 13 | 7.1 | 8.1 |

While the invention has been described by reference to specific embodiments, this was for purposes of illustration only. Numerous alternative embodiments will be apparent to those skilled in the art and are deemed to be within the scope of the invention.

What is claimed is:

1. The compound which is 1-[4-(2-methoxyphenyl) piperazin-1-yl]-3-(2,5-dioxopyrrolidin-1-yl)propane or its hydrochloride salt.

2. The compound which is 1-[4-(2-methoxyphenyl) piperazin-1-yl]-3-(2,6-dioxopiperidin-1-yl)propane or its hydrochloride salt.

3. The compound which is 1-[4-(2-fluorophenyl) piperazin-1-yl]-3-(2,6-dioxopiperidin-1-yl)propane or its hydrochloride salt.

4. The compound which is 1-[4-(2-methylphenyl) piperazin-1-yl]-3-(2,6-dioxopiperidin-1-yl)propane or its hydrochloride salt.

5. The compound which is 1-[4-(2-pyridyl)piperazin-1-yl)-3-(2,6-dioxopiperidin-1-yl)propane or its hydrochloride salt.

6. The compound which is 1-[4-(2-Methoxyphenyl) piperazin-1-yl]-3-[2,5-dioxo-3-phenyl-pyrolidin-1-yl] propane or its hydrochloride salt.

7. The compound which is 1-[4-(Phenyl)piperidin-1-yl]-3-[2,5-dioxopyrolidin-1-yl]propane or its hydrochloride salt.

8. A pharmaceutical composition comprising the compound of any of claims 1, 2, 3, 4, 5, 6, or 7 pharmaceutically acceptable carrier.

* * * * *